US011471053B2

(12) United States Patent
Bigot et al.

(10) Patent No.: US 11,471,053 B2
(45) Date of Patent: Oct. 18, 2022

(54) THERMAL THERAPY WITH DYNAMIC ANATOMICAL BOUNDARIES USING MRI-BASED TEMPERATURE UNCERTAINTY MAPS

(71) Applicant: Profound Medical Inc., Mississauga (CA)

(72) Inventors: Alexandre Bigot, Toronto (CA); Patrick Leonard, Toronto (CA); Ron Kurtz, Oakville (CA)

(73) Assignee: Profound Medical Inc., Mississauga (CA)

( * ) Notice: Subject to any disclaimer, the term of this patent is extended or adjusted under 35 U.S.C. 154(b) by 1180 days.

(21) Appl. No.: 15/797,075

(22) Filed: Oct. 30, 2017

(65) Prior Publication Data

US 2019/0125253 A1    May 2, 2019

(51) Int. Cl.
| | | |
|---|---|---|
| *A61B 5/01* | (2006.01) | |
| *A61B 5/00* | (2006.01) | |
| *A61N 7/02* | (2006.01) | |
| *A61B 5/055* | (2006.01) | |
| *A61B 34/10* | (2016.01) | |
| *A61B 90/00* | (2016.01) | |
| *A61B 17/00* | (2006.01) | |
| *G16H 40/60* | (2018.01) | |

(52) U.S. Cl.
CPC ............ *A61B 5/0036* (2018.08); *A61B 5/015* (2013.01); *A61B 5/055* (2013.01); *A61B 5/4381* (2013.01); *A61B 34/10* (2016.02); *A61N 7/02* (2013.01); *A61B 2017/00084* (2013.01); *A61B 2090/374* (2016.02); *G16H 40/60* (2018.01)

(58) Field of Classification Search
None
See application file for complete search history.

(56) References Cited

U.S. PATENT DOCUMENTS

| | | | |
|---|---|---|---|
| 7,771,418 B2 | 4/2010 | Chopra et al. | |
| 7,993,289 B2* | 8/2011 | Quistgaard | A61B 8/00 601/2 |
| 9,119,550 B2* | 9/2015 | Lee | A61B 8/5261 |
| 9,554,770 B2* | 1/2017 | Fan | G01S 7/52036 |
| 9,750,411 B2* | 9/2017 | Gross | A61B 5/7275 |
| 9,971,004 B2* | 5/2018 | Kurtz | A61B 5/4381 |
| 2002/0180438 A1 | 12/2002 | Froundlich et al. | |
| 2004/0010191 A1 | 1/2004 | Yatsui | |
| 2005/0154431 A1* | 7/2005 | Quistgaard | A61B 8/4218 607/96 |
| 2007/0239062 A1 | 10/2007 | Chopra et al. | |
| 2010/0286516 A1* | 11/2010 | Fan | A61B 8/08 600/438 |

(Continued)

OTHER PUBLICATIONS

ISA, "International Search Report", PCT/IB2017/001479, dated Jul. 11, 2018.

*Primary Examiner* — Luther Behringer
(74) *Attorney, Agent, or Firm* — Intrinsic Law Corp.

(57) ABSTRACT

Temperature uncertainty maps are calculated based on a rolling window of temperature maps, which is updated as new temperature maps are generated. The rolling window mitigates the effect of transient motion during a thermal therapy procedure. A clinician or an automated control system can then update a portion of an anatomical boundary or the thermal therapy applicator center based on the temperature uncertainty map.

12 Claims, 12 Drawing Sheets

(56) References Cited

U.S. PATENT DOCUMENTS

| | | |
|---|---|---|
| 2011/0137147 A1 | 6/2011 | Skliar et al. |
| 2013/0261429 A1* | 10/2013 | Lee .................. A61B 5/0035 |
| | | 600/411 |
| 2015/0038883 A1 | 2/2015 | Kurtz et al. |
| 2015/0080705 A1 | 3/2015 | Partanen et al. |
| 2015/0087963 A1 | 3/2015 | Tyc et al. |

* cited by examiner

THERMAL THERAPY WITH DYNAMIC ANATOMICAL BOUNDARIES USING MRI-BASED TEMPERATURE UNCERTAINTY MAPS

TECHNICAL FIELD

This invention relates to thermal therapy delivered by a treatment apparatus to a target tissue within an anatomical boundary based on dynamic thermal uncertainty maps derived from MRI thermometry systems and data.

BACKGROUND

The use of magnetic resonance imaging (MRI) to obtain temperature related data in a tissue ablation procedure is discussed e.g., in Chopra (U.S. Pat. No. 7,771,418), which is hereby incorporated by reference. MRI thermometry, the resulting temperature measurements and temperature uncertainty maps thereof, and related considerations are discussed by the present applicant, e.g., in published application US2015/0038883A1, incorporated herein by reference as well.

Generally, temperature measurements using MRI methods are subject to errors from a variety of sources known to those skilled in the art. When temperature measurements are used as part of a feedback system for thermal energy delivery, these errors contribute to unintended heating or lack of heating of the target region. Errors in temperature measurements during treatment using MRI methods include transient motion, such as bulk patient motion, localized prostate motion (e.g., due to heating of muscles or nerves), and/or rectum displacement. For example, transient motion can cause significant errors in temperature measurement, which are currently addressed by waiting (e.g., for 20 minutes) for the measured body temperature to return to an approximately constant value. This results in less than optimal treatment sessions from a patient comfort perspective, as well as reduced patient throughput or less economical use of the MRI-thermal therapy treatment facility, personnel and equipment.

SUMMARY

The method described here calculates and displays the regions where the temperature can be reliably measured. The clinician then can make an informed decision to treat these regions or plan a treatment to avoid them based on the sensitivity of surrounding structures to unintended heating.

An aspect of the invention is directed to a method for dynamically delivering thermal therapy to a target volume within a patient's body. The method comprises determining an anatomical boundary corresponding to the target volume for delivery of thermal therapy thereto; using a thermal therapy applicator comprising an ultrasound transducer array, delivering a thermal therapy dose to said target volume; in a computer, receiving N sets of temperature data for pixels corresponding to a portion of a patient's body, each set of temperature data corresponding to a respective capture time of phase images captured using a magnetic resonance imaging (MRI) device, wherein N is greater than or equal to M, and M is a rolling capture time window; in the computer, for each of the past M capture times, determining a corrected temperature at each pixel; in the computer, for each pixel, calculating a temperature uncertainty based on said corrected temperature at each of the past M capture times; and in the computer, modifying a portion of the anatomical boundary only when the temperature uncertainty for the portion of the anatomical boundary is below a threshold temperature uncertainty.

In one or more embodiments, the temperature uncertainty corresponds to a standard deviation of said corrected temperature at each pixel across the past M capture times. In one or more embodiments, the method further comprises pausing the delivery of the thermal therapy dose before modifying the portion of the anatomical boundary. In one or more embodiments, the method further comprises modifying a location of a thermal therapy applicator center.

In one or more embodiments, the method further comprises, in the computer, validating the anatomical boundary to confirm that the temperature uncertainty for the portion of the anatomical boundary is below the threshold temperature uncertainty. In one or more embodiments, the method further comprises, in the computer, generating an alert when the temperature uncertainty for the portion of the anatomical boundary is greater than the threshold temperature uncertainty.

In one or more embodiments, the method further comprises, in the computer, calculating a standard deviation at each point along the anatomical boundary across the past M capture times. In one or more embodiments, the method further comprises, in the computer, generating a temperature uncertainty map, the temperature uncertainty map including the temperature uncertainty for each pixel. In one or more embodiments, the method further comprises displaying the temperature uncertainty map on a display coupled to the computer.

In one or more embodiments, the method further comprises detrending the corrected temperature at each pixel across the past M capture times to form detrended temperature data. In one or more embodiments, the method further comprises performing a linear regression of the corrected temperature at each pixel across the past M capture times. In one or more embodiments, the method further comprises calculating the standard deviation of the detrended temperature data at each pixel. In one or more embodiments, the method further comprises determining the temperature uncertainty based on the standard deviation of the detrended temperature data at each pixel.

In one or more embodiments, the method further comprises, in the computer, receiving a new set of temperature data for pixels corresponding to the portion of a patient's body; and calculating an updated temperature uncertainty based on the past M capture times, the past M capture times including the new set of temperature data.

BRIEF DESCRIPTION OF THE DRAWINGS

For a fuller understanding of the nature and advantages of the present invention, reference is made to the following detailed description of preferred embodiments and in connection with the accompanying drawings, in which.

DETAILED DESCRIPTION

The present disclosure provides systems and methods for overcoming the effects of and avoiding errors due to such temperature measurement uncertainties. Accordingly, improved accuracy and efficiency of delivery of MRI-guided thermal therapies is made possible. One application for such therapies is in treating the diseased male prostate.

Embodiments of the invention relates to dynamically changing and validating the prostate contour and ultrasound applicator center during treatment. The prostate contour and/or applicator center may need to be adjusted (manually or automatically) during treatment due to transient motion, which can cause the baseline treatment parameters (e.g., prostate boundary and ultrasound applicator center) to be invalid. Examples of transient motion include bulk patient motion, localized prostate motion (e.g., due to heating of muscles or nerves), and/or rectum displacement. The prostate contour may also need to be adjusted if noise corrupts some sections of the boundaries. For example, there may be a low signal region due to gas in the rectum or due to transient motion. Further, the prostate contour may need to be adjusted to avoid treatment of a region (e.g., a section was treated once and retreatment is not desired). The ultrasound applicator center may need to be adjusted because alignment of the ultrasound applicator center was incorrect in treatment planning or due to transient motion.

To account for transient motion, the temperature and temporal temperature uncertainty at each pixel are calculated retrospectively at a given data capture time over a rolling time window during treatment.

Figure 1:
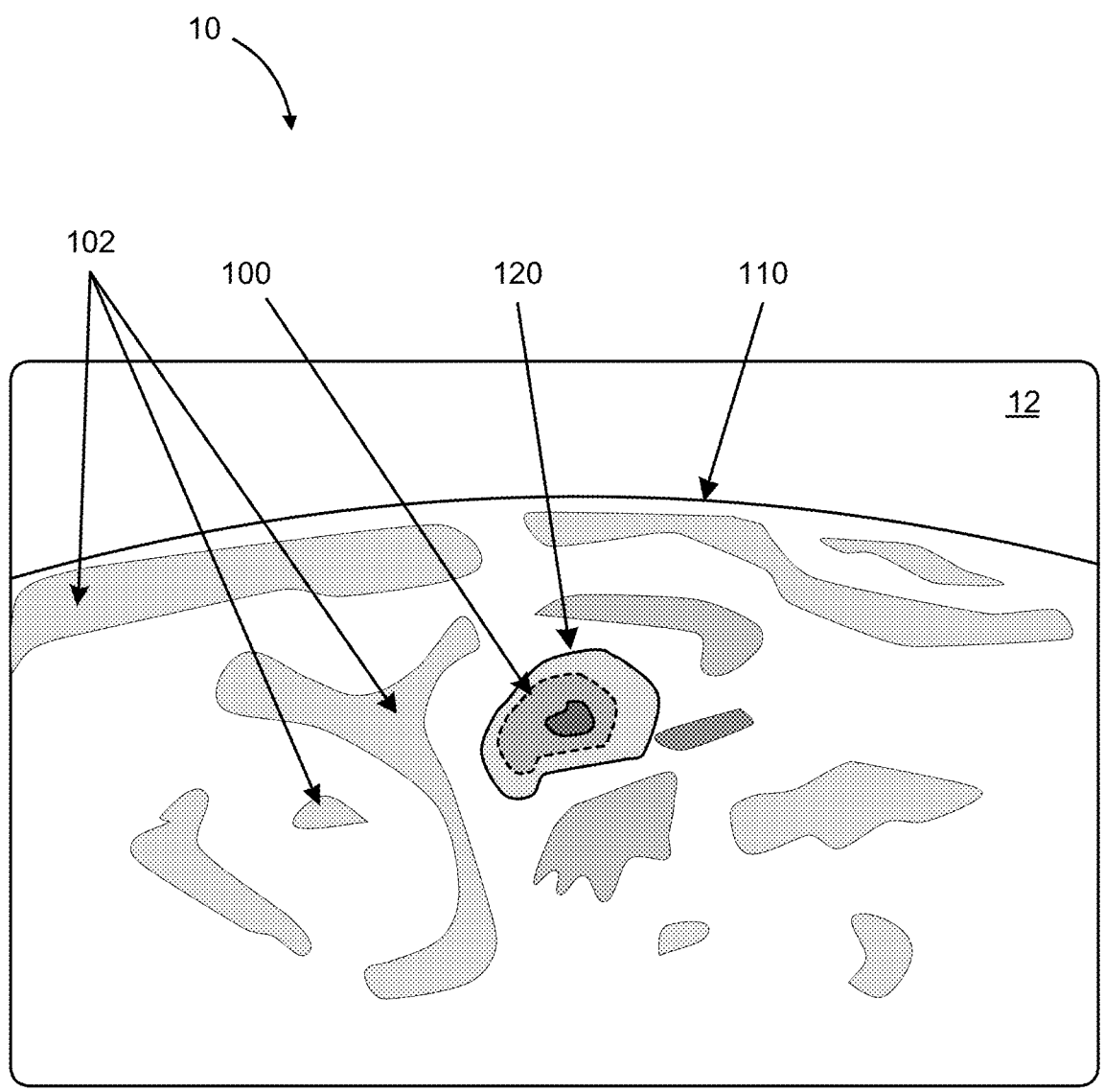
FIG. 1 illustrates a representation of a cross section of a MRI temperature uncertainty map and showing the prostate boundary and target boundary.

FIG. 1 illustrates a cross sectional view taken using an imaging modality such as MRI imaging of a portion of a patient's body in the vicinity of a treatment target volume. The scene shown includes for example a visual output device such as a computer monitor screen 10 or application window of a computer application program for displaying an image 12. The surface of the patient's body (e.g., the surface of his abdomen) is shown at 110 while various zones 102 in the patient's body are shown by a visual representation of their temperatures and/or temperature uncertainties within image 12. The zones 102 can be displayed on screen 10 as colored contours, contour plots, gray scale intensities or other visual representations of the temperature uncertainty. The values plotted and represented are determined as described below.

The image 12 shows a boundary of a target volume such as a male prostate or portion thereof 120. This is an outline on image 12, which can be computer-drawn or drawn with the assistance of an operator on the screen 10. A treatment target boundary 100 is further shown on the image 12, which can be a contour of another color, a dashed contour, or other representation. The target boundary 100 is the intended boundary within which the energy of the thermal treatment process is substantially controlled to a set-point temperature (or thermal dose) ensuring rapid and sufficient cell death of diseased cells within the interior of the volume defined by the target boundary 100. Heat can be conducted outside the target boundary 100 out to the boundary of the prostate 120, which can be measured and controlled to achieve appropriate thermal therapy while reasonably avoiding damage to non-diseased tissues and organs proximal to said diseased locations. Tissues and organs outside the target boundary, even if heated, will not exceed lethal thermal dose or temperature limits.

Methods for determining and controlling the intensity of the thermal therapy treatment as a function of the temperature or desired temperature at such a boundary 100 are described by the present inventors in publications and patent applications available to the public, which are hereby incorporated by reference.

In all, FIG. 1 thus shows a temperature uncertainty map. Three-dimensional representations of the same can be constructed from additional layers, slices or cross-sectional views like that shown in FIG. 1. The methods described herein can therefore be generalized to three dimensional space by stacking slices such as shown in FIG. 1 side by side to form a 3D volume without loss of generality.

Figure 2:
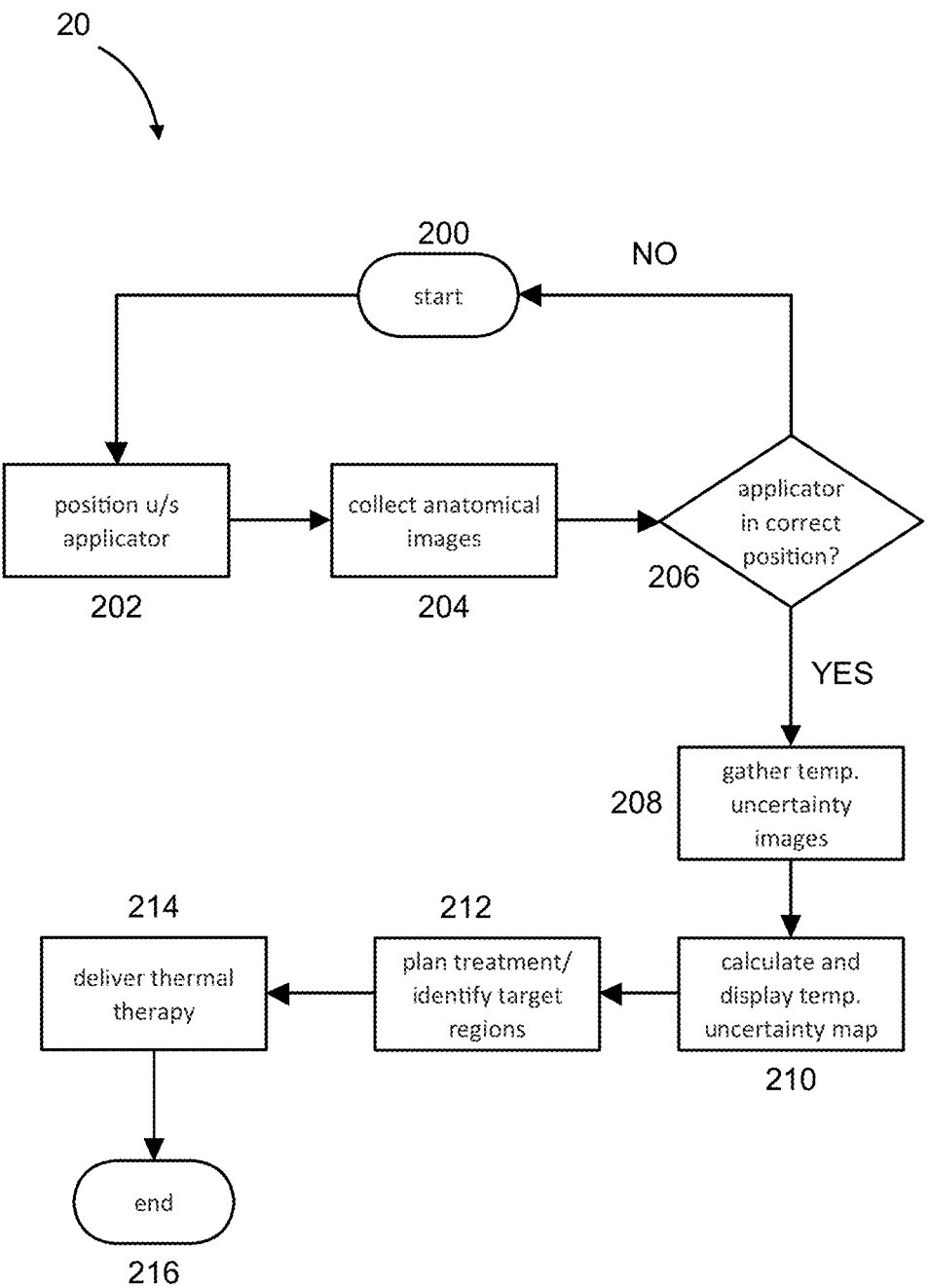
FIG. 2 illustrates an exemplary treatment workflow process.

FIG. 2 illustrates an exemplary process 20 enabling thermal treatment in a MRI-guided environment and accounting for temperature uncertainty in the MRI thermometry portion of the process. The process starts at 200 and an automated or operator-driven positioning of the thermal therapy device in or on the patient is done at step 202. In an example, an ultrasound (u/s) thermal therapy applicator is inserted trans-urethrally into a diseased male prostate organ and positioned so as to deliver thermal therapy to the diseased organ. In another aspect, the patient is placed in a MRI imaging volume or machine bore and temperature scans using MRI thermometry are obtained, slice by slice, through a target region to generate thermal imagery and/or temperature uncertainty maps of the target region.

Anatomical images of the patient or portion of the patient in the vicinity of the target region are obtained at step 204. The system can automatically or semi-automatically determine whether the thermal therapy applicator is in the correct position to deliver the desired thermal therapy to the target region at 206. If not, the process returns to position the thermal therapy applicator at 202.

Once the thermal therapy applicator device is in the correct position, temperature uncertainty images like those depicted in FIG. 1 are collected at 208. A memory or digital storage apparatus can be used to store the data so collected for analysis or other purposes.

The system next calculates and displays the temperature uncertainty maps as depicted above at step 210. These are preferably output to a computer output or display device such as a computer workstation monitor connected to the imaging and therapy device in an overall thermal therapy control system.

Using the temperature data and temperature uncertainty maps, a thermal therapy treatment plan is determined and target points or regions are identified at step 212.

The thermal therapy itself is delivered from a thermal therapy applicator, e.g., an ultrasound transducer array device in or proximal to the desired target region at step 214. During thermal therapy, additional temperature uncertainty images are gathered and displayed, as discussed below.

Once the thermal therapy procedure is complete, the system or operator terminates the process 20 at 216.

Figure 3:
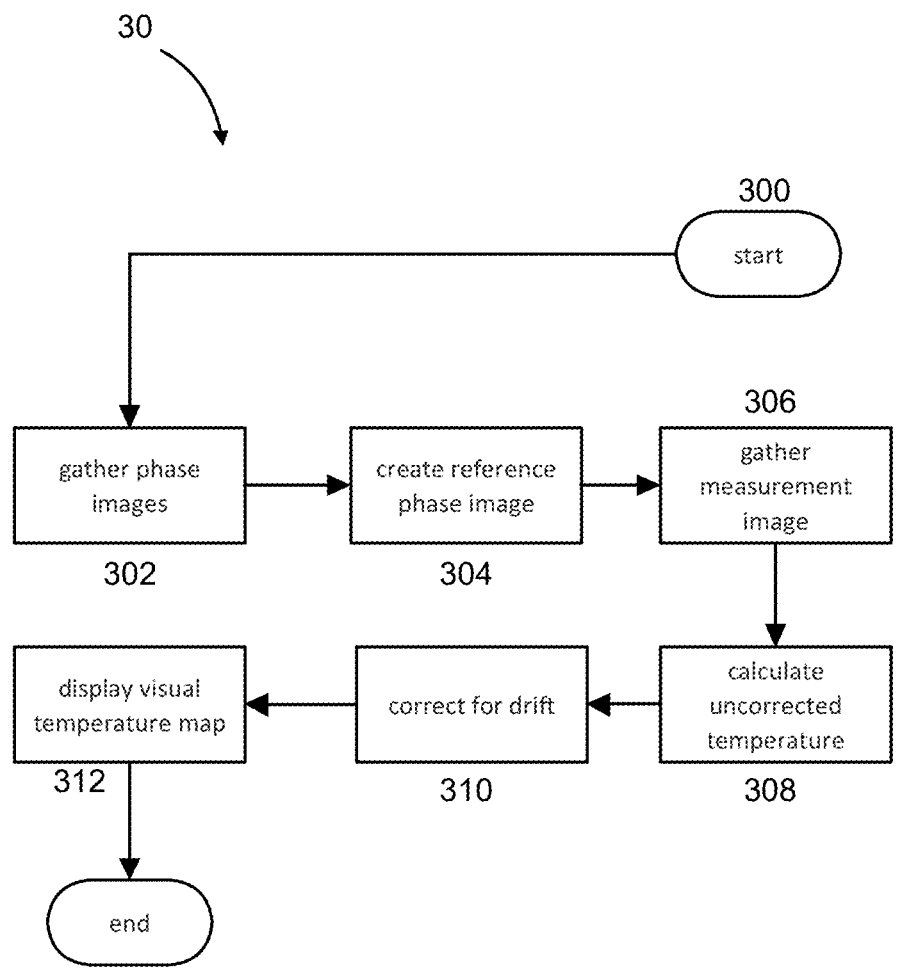
FIG. 3 illustrates an exemplary process for calculating a temperature uncertainty map.

FIG. 3 illustrates another set of steps in an exemplary computer-implemented method 30 for gathering images in the context of image-guided thermal therapy, making appropriate corrections and generating outputs for use in that context.

The process starts at 300 and one or more phase images are gathered from a nuclear magnetic resonance or MRI device in which a patient is placed. In an embodiment, several (e.g., three to ten) phase images are gathered at step 302 and stored in a machine-readable storage device such as a computer memory device. The MRI device can be configured, arranged, programmed and operated so as to run a sequence to output the magnitude and phase images in real time. The output images are output through a signal connection or network connection as desired, for example to another computer device, coupled to the MRI device, where subsequent computations and processing of the MRI data can be carried out.

In an example, an EPI sequence is used to gather the channel uncombined phase images. Other sequences can be used as would be understood by those skilled in the art, for example a GRE sequence.

In some thermal therapies using an ultrasound transducer system, multiple ultrasound transducer elements are deployed in an ultrasonic array placed within the diseased tissue volume. For multi-transducer ultrasound therapy systems, multiple image slices can be taken such that one image slice is taken per ultrasound transducer per therapy applicator system. In yet another aspect, a monitoring slice image can be taken at either end of the imaging slices for full monitoring. The sequence is set in an embodiment to automatically repeat so that stacks of phase images are generated continuously throughout the thermal therapy treatment.

A reference phase image is created at step 304 using data from the gathered phase images in the previous step. This reference phase image is the phase image prior to initiating heating from the thermal therapy procedure. To increase signal to noise, the reference phase image is calculated as the average phase over several (e.g., 5) reference images for each pixel in the image.

A measurement image is collected at step 306 prior to and/or during the thermal therapy procedure. The system then calculates uncorrected temperatures at step 308. In an example, a weighted sum of the phase differences across all channels is calculated and scaled so as to determine temperatures. In an aspect, an MRI device can be programmed to output the combined phase for all coils. In this case the system only requires to calculate the phase difference from the reference image to be scaled to output the temperature in a region of interest.

At step 310 the system corrects for drift. As mentioned before, the drift could be due to temporal changes or drift in the main BO magnetic field of the MRI machine. The drift could result in erroneous (typically lower) temperature measurements if not corrected for. Therefore, according to a present aspect, we correct for such drift effects at one or more areas of the image. The temperature at these areas is assumed to be that of the patient's body's core temperature, which substantially does not change throughout a therapy treatment. A two-dimensional linear interpolation of the drift is calculated for each measurement slice image and added to the temperature at each pixel in the image to generate a drift-corrected temperature image.

In step 312, a visual temperature map is displayed on a display coupled to the computer.

Figure 4:
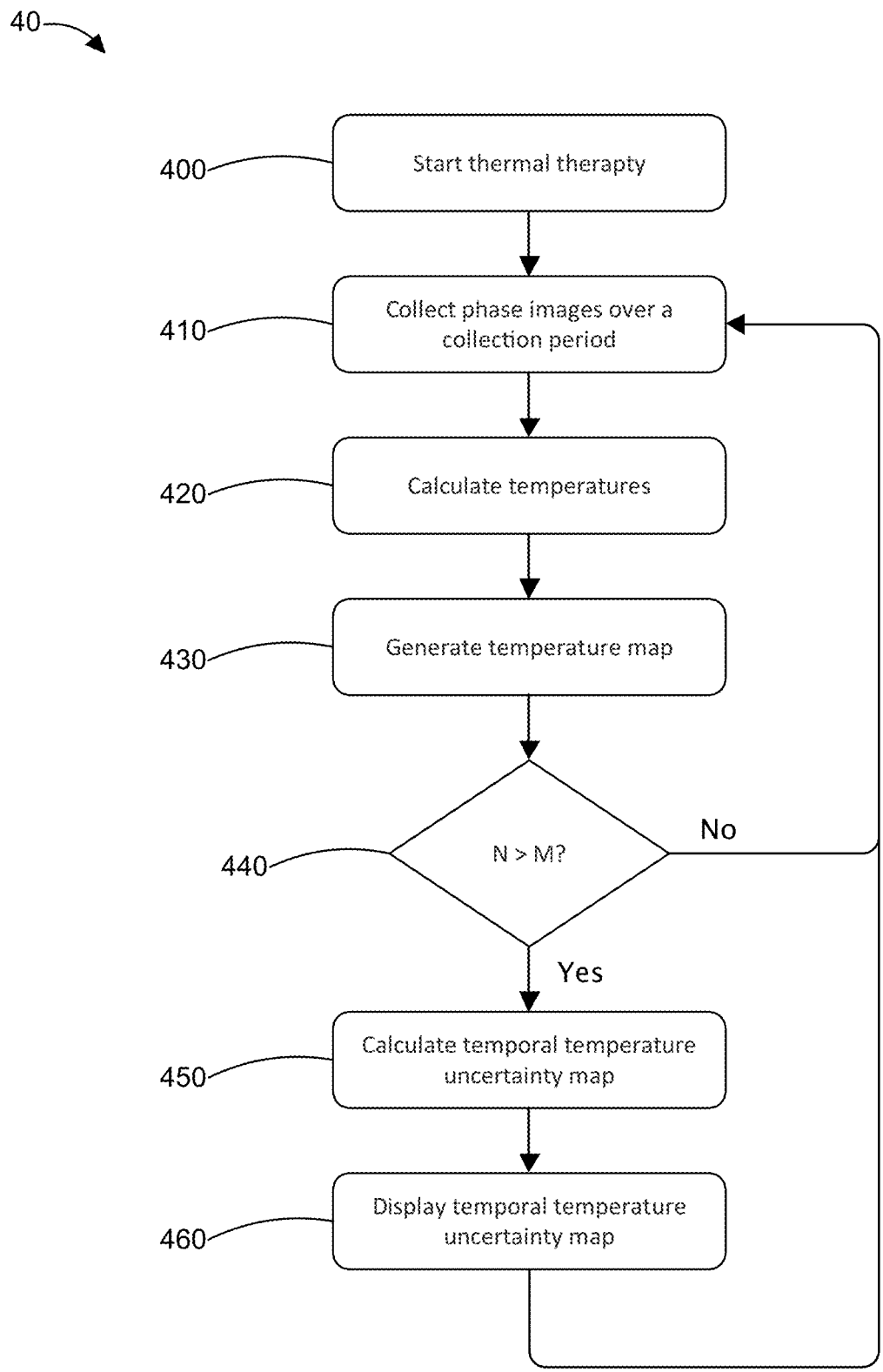
FIG. 4 is a flow chart for dynamically calculating a temperature uncertainty map of temperatures in a target volume.

FIG. 4 is a flow chart 40 for dynamically calculating a temperature uncertainty map of temperatures in a target volume. In step 400, thermal therapy is delivered from a thermal therapy applicator (e.g., an ultrasound transducer array device in or proximal to the desired target region), as discussed above. The thermal therapy can be delivered with a treatment plan, for example as discussed above with respect to FIG. 2. In step 410, MRI phase images are collected from a MRI device during a collection period (e.g., a dynamic). The dynamic or collection period can be based on time (e.g., 3 to 5 seconds) and/or on the number of phase images collected (e.g., 25 to 50 phase images). In step 420, the corrected temperature at each pixel is determined by calculating the phase difference between (a) the average phase over the phase image collection period (the average measurement phase) and (b) the average phase over several (e.g., 5) references images for each pixel in the image (e.g., as discussed above) and then correcting for drift, similar to the manner described in FIG. 3. In step 430, a temperature map is generated and optionally displayed to the user, for example as discussed above with respect to FIG. 3.

In step 440, the computer determines the number of temperature maps that are stored in memory. If the number of temperature maps (N) is less than M, the flow chart returns to step 410 to collect additional MRI phase images during another collection period (and generate corresponding temperature maps). This process repeats until N is greater than or equal to M, where M is a rolling window of temperature maps used to calculate a temperature uncertainty map, as discussed below. Thus, M is an integer greater than or equal to 2, and preferably is at least 5.

When N is greater than or equal to M, the flow chart 40 proceeds to step 450 where the temporal temperature uncertainty map is calculated. The temporal temperature uncertainty map is formed by calculating the standard deviation of the temperature at each pixel across the last M temperature maps. For example, if there are 10 temperature maps (N=10) and the rolling window of temperature maps is 5 (M=5), only the last 5 temperature maps are used to calculate the temporal temperature uncertainty map. Alternatively, each of the past temperature maps is used based on a weighted average, with the more recent temperature maps having a higher weight than the older temperature maps.

In step 460, the temporal temperature uncertainty map is displayed visually on a display coupled to the computer. The temporal temperature uncertainty map can be color-coded according to different temperature uncertainty ranges. For example, shades of blue can be assigned to temperature uncertainties below a first threshold value (e.g., less than 2° C.), shades of yellow and red for temperature uncertainties between the first threshold and a second threshold (e.g., between 2-4° C.), and shades of purple for temperature uncertainties greater than the second threshold (e.g., greater than 4° C.).

After step 460, the flow chart 40 returns to step 410 to collect additional MRI phase images during the next collection period. In the next iteration through the flow chart 40, a new temperature map (N+1) is generated and the temperature uncertainty map is calculated based on the temperature maps in the current rolling window of temperature maps M. In other words, in the next iteration, the current rolling window of temperature maps M includes the latest temperature map (N+1) but does not include the oldest temperature map used in the last iteration. Alternatively, all temperature maps are used based on a weighted average, as discussed above.

In some embodiments, a linear regression is performed on the temperature at each pixel across the rolling window M, which can reduce the impact of heating (or cooling) on the temperature uncertainty map. The temperature uncertainty map is then calculated in step 450 using the de-trended data.

The rolling window M can reduce the impact of transient motion on the temperature uncertainty map. For example, transient motion may cause a shift in the temperatures in a given temperature map because, for example, the ultrasound applicator center has moved with respect to the baseline image. However, the impact of such a shift can be reduced over time by comparing the shifted temperature map with subsequent temperature maps which may also have a shift in temperature.

Figure 5A:
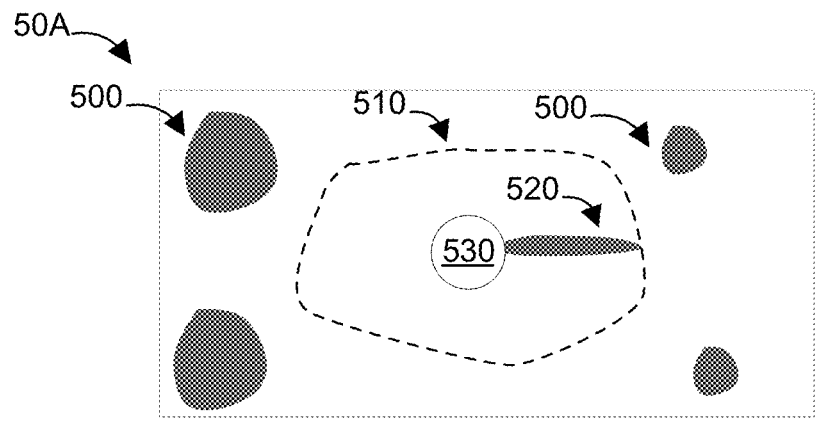
FIGS. 5A, 5B, and 5C illustrate examples of temperature uncertainty maps that may be produced according to the flow chart of FIG. 4.
Figure 5B:
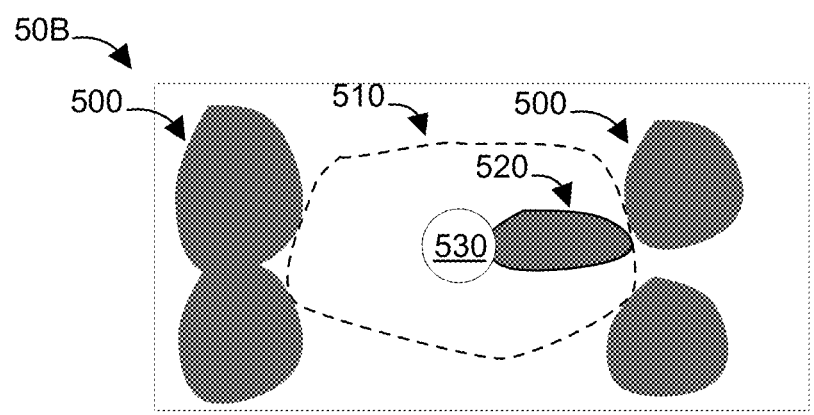
Figure 5C:
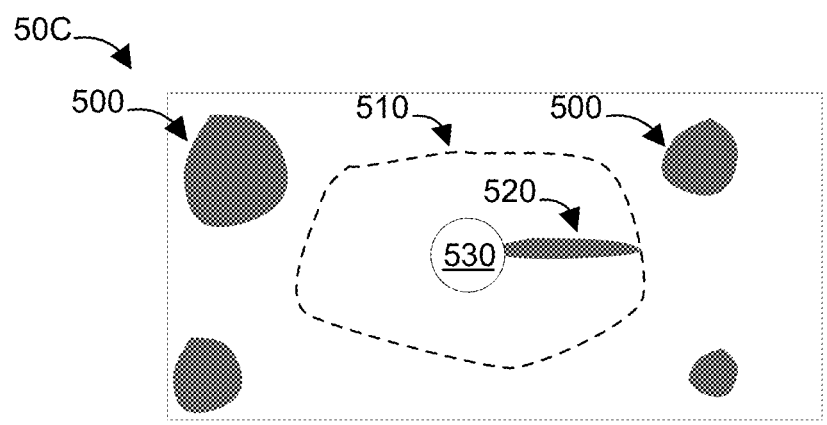

Examples of temperature uncertainty maps that may be produced according to flow chart 40 are illustrated in FIGS. 5A-5C. FIG. 5A illustrates a first temperature uncertainty map 50A corresponding to a first time collection period (e.g., time period 10). In temperature uncertainty map 50A, there are few regions of high temperature uncertainty 500. The remainder of the temperature uncertainty map 50A has low temperature uncertainty. The regions of high temperature uncertainty 500 are disposed outside of the prostate boundary 510 and inside the prostate boundary 510 at flame 520, which corresponds to the thermal therapy generated by applicator 530.

FIG. 5B illustrates a temperature uncertainty map 50B corresponding to a second time collection period (e.g., time period 20), which occurs after transient motion. As can be seen the regions of high temperature uncertainty 500 are larger in temperature uncertainty map 50B than in temperature uncertainty map 50A. In addition, the regions of high temperature uncertainty 500 are disposed adjacent to the prostate boundary 510. The system or operator can modify any location of prostate boundary 510 or applicator center 530 subject to computer validation that the modified locations are below a threshold value (e.g., 2° C.).

FIG. 5C illustrates a temperature uncertainty map 50C corresponding to a third time collection period (e.g., time period 30). As can be seen, the regions of high temperature uncertainty 500 are reduced in temperature uncertainty map 50C after a time period due to the rolling time window M discussed herein.

Figure 6:
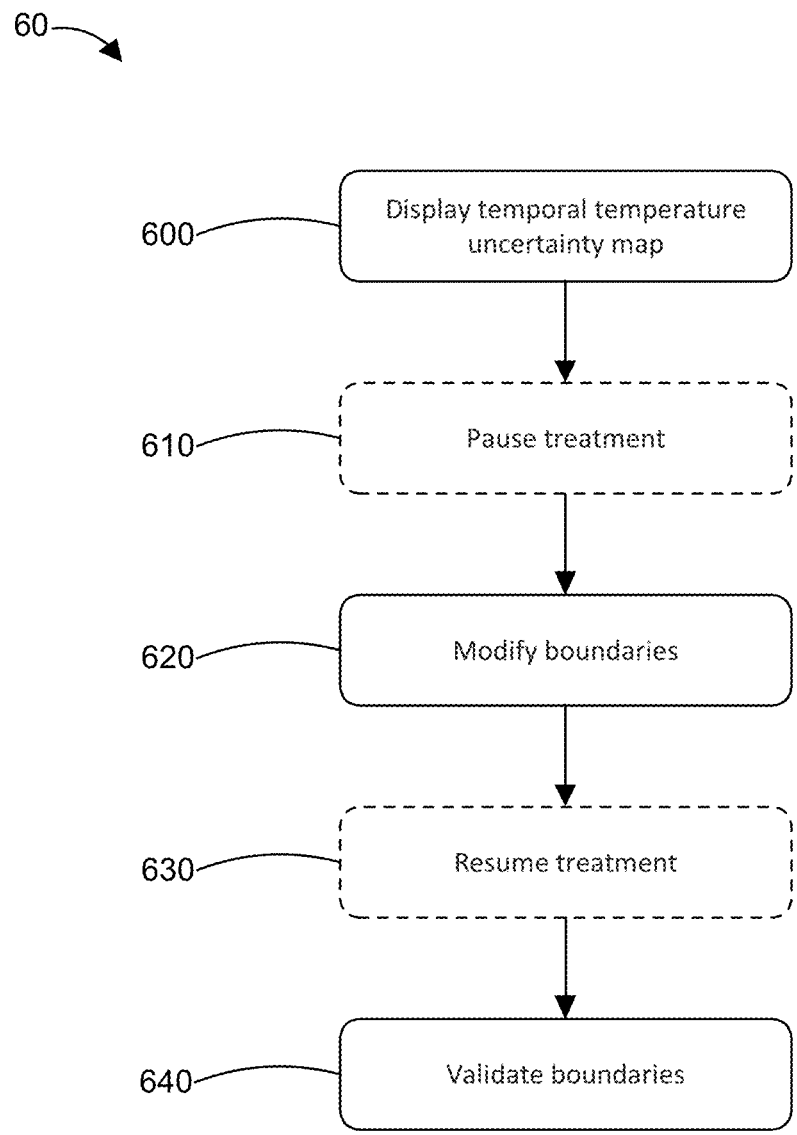
FIG. 6 is a flow chart of a method for updating the prostate boundary.

FIG. 6 is a flow chart 60 of a method for updating the prostate boundary. In step 600, the temporal temperature uncertainty map is displayed on a display coupled to the computer. In optional step 610, the operator manually or the computer automatically pauses treatment. Treatment can be paused, for example, to provide time for additional time collection periods to reduce the temperature uncertainty (e.g., as discussed above). In step 620, the operator manually or the computer automatically modifies the prostate boundary and/or the position of the ultrasound applicator center (e.g., to compensate for transient motion). In optional step 630, the operator manually or the computer automatically resumes treatment. In step 640, the computer validates the new prostate boundary to confirm that the prostate boundary has not been modified at a location of high temperature uncertainty.

Figure 7:
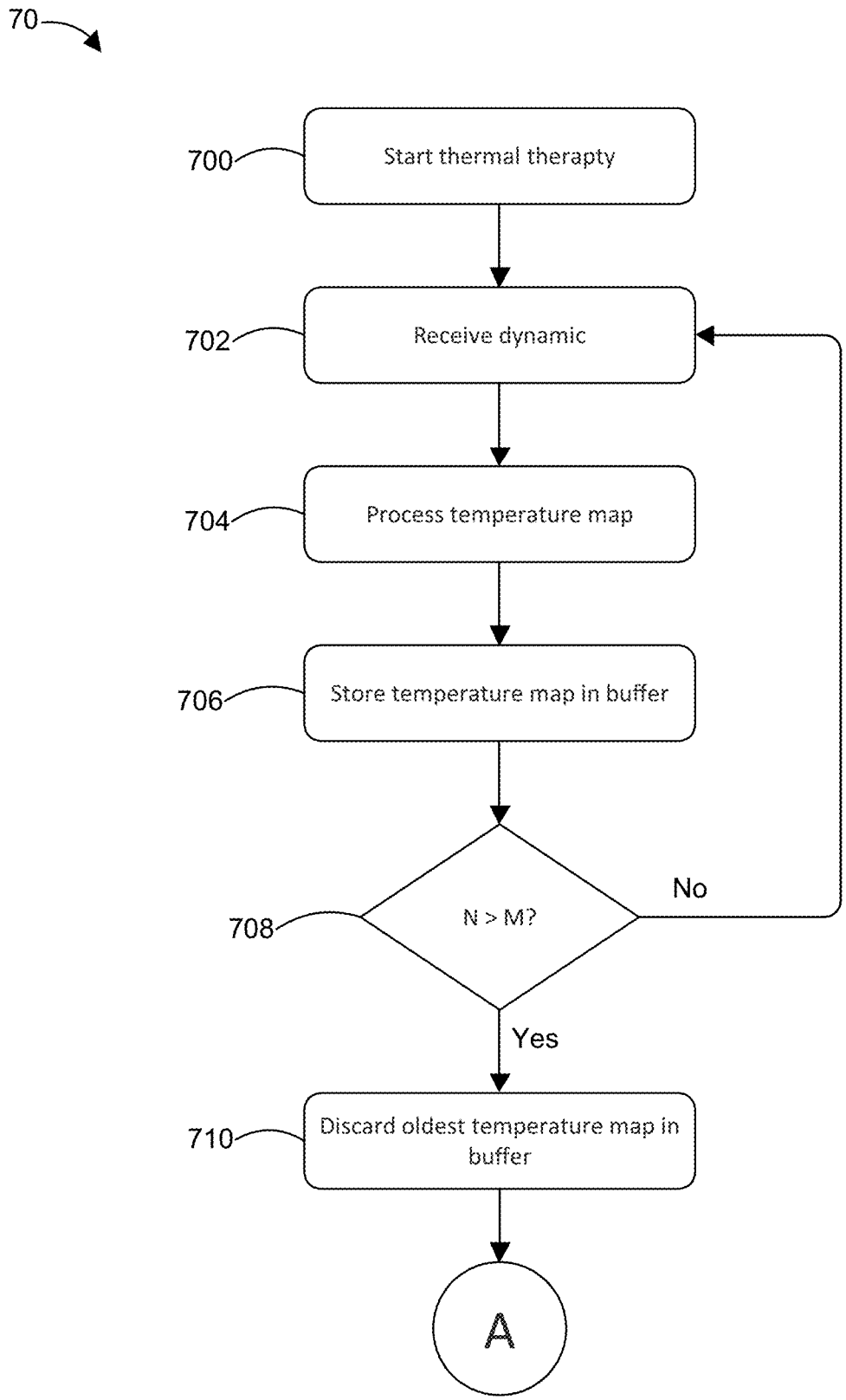
FIGS. 7, 8, 9, and 10 illustrate a flow chart for dynamically calculating a temperature uncertainty map of temperatures in a target volume.

FIG. 7 is a flow chart 70 for dynamically calculating a temperature uncertainty map of temperatures in a target volume. In step 700, thermal therapy is delivered from a thermal therapy applicator (e.g., an ultrasound transducer array device in or proximal to the desired target region), as discussed above. The thermal therapy can be delivered with a treatment plan, for example as discussed above with respect to FIG. 2. In step 702, MRI phase images are collected from a MRI device during a collection period (e.g., a dynamic). The dynamic or collection period can be based on time (e.g., 3 to 5 seconds) and/or on the number of phase images collected (e.g., 25 to 50 phase images). In step 704, the phase images collected during the dynamic are processed to form a temperature map (e.g., as described above with respect to FIG. 4). In step 706, the temperature map is stored in a buffer having a width of M temperature maps (corresponding to M dynamics), where M is a rolling window of temperature maps or dynamics used to calculate a temperature uncertainty map. Thus, M is an integer greater than or equal to 2, and preferably is at least 5.

If the number of temperature maps or dynamics (N) is less than or equal to M, the flow chart returns to step 702 to receive another dynamic and to process a corresponding temperature map in step 704, which is then added to the buffer in step 706. This process repeats until N is greater than M in step 708.

When N is greater than M, the flow chart 70 proceeds to step 710 where the oldest temperature map (corresponding to the oldest dynamic) is discarded from the buffer. Thus, the buffer only contains the last M temperature maps or dynamics. After step 710, the flow chart 70 proceeds to placeholder A, which also appears in FIG. 8. It is noted that the acquisition and processing of new dynamics occurs throughout flow chart 70, and thus the temperature uncertainty maps can be updated dynamically during any step of flow chart 70.

Figure 8:
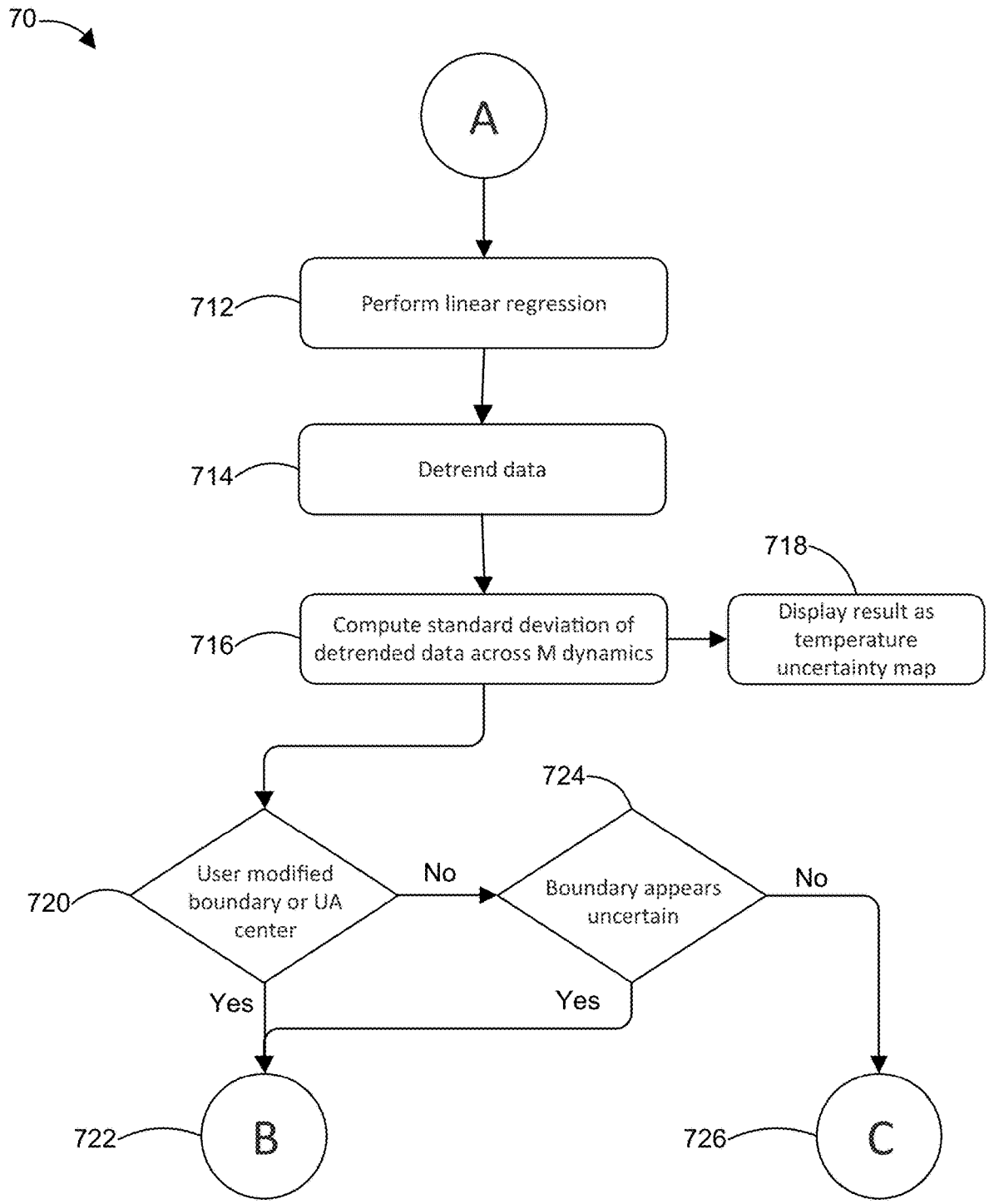
Figure 12:
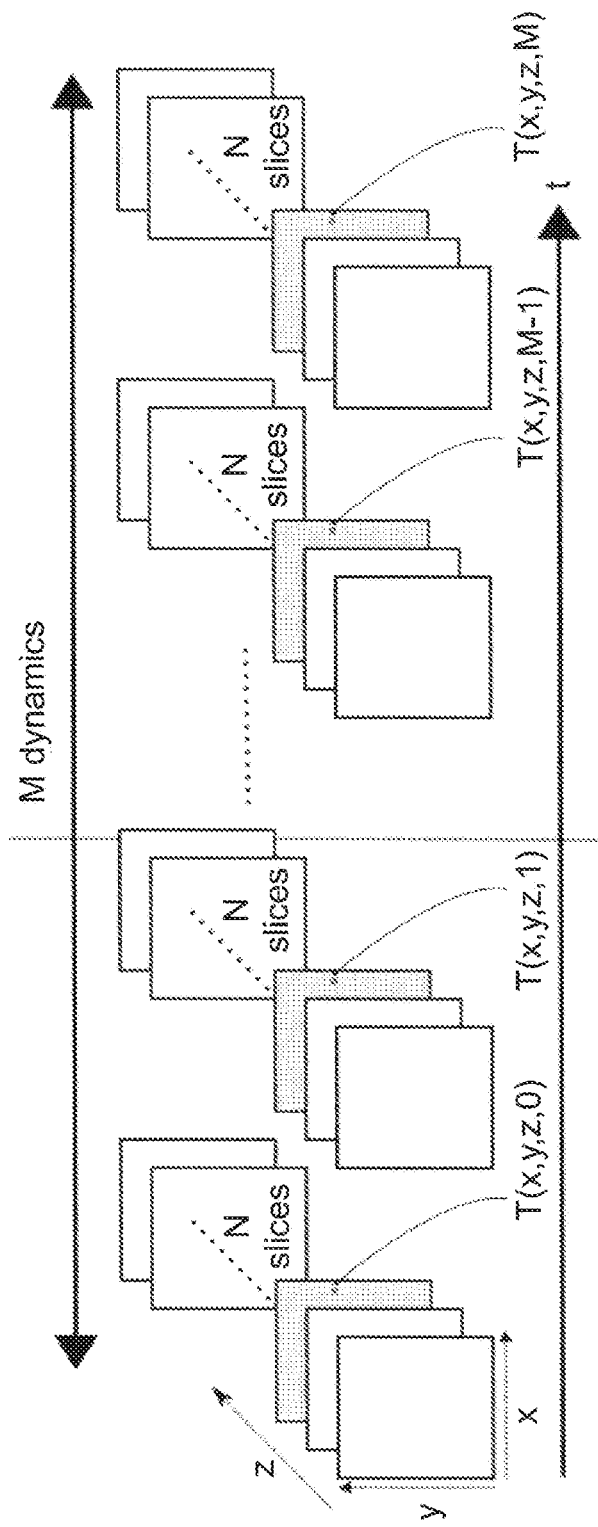
FIG. 12 illustrates an example of a coordinate system used in some embodiments.

Starting at placeholder A on FIG. 8, the flow chart 70 proceeds to step 712 to perform a linear regression (e.g., a first order linear regression) for each pixel, slice, and dynamic in the buffer stack. The first order linear regression can be calculated using the formula $T_{estimate}(x,y,z)=a1(x,y,z)t+b1(x,y,z)+\varepsilon$, which estimates the temperature increase for each pixel across the last M dynamics as a linear trend. In this equation, x and y refer to the coordinates of the pixel, z refers to the coordinate (e.g., slice number) across the volume of a dynamic constituted of N slices, a1 corresponds to the slope of the first order regression, b1 corresponds to the intercept of the first order regression, and $\varepsilon$ corresponds to the noise of the data. The coordinates x, y, and z are also illustrated in FIG. 12.

Figure 11:
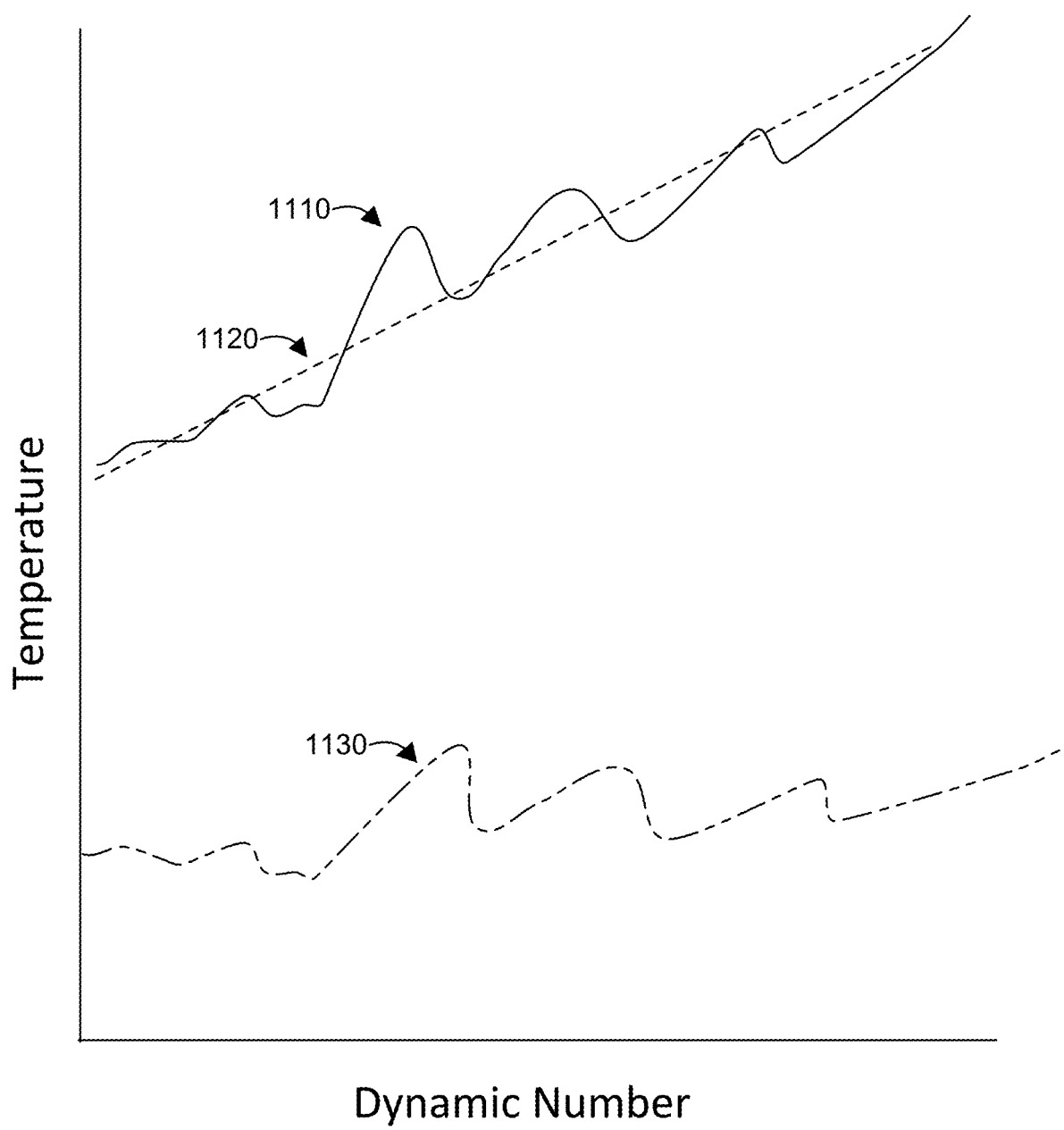
FIG. 11 is a graph that illustrates the effect of detrending temperature data.

In step 714, the data is detrended according to the formula $T_{detrended}(x,y,z)=T(x,y,z)-T_{estimate}(x,y,z)$, where $T(x,y,z)$ is the temperature measured by MRI thermometry and $T_{estimate}(x,y,z)$ is calculated in step 712. An example of a graph that illustrates the effect of detrending temperature data is illustrated in FIG. 11, where line 1110 represents the measured heated data of a pixel, line 1120 represents a first order fit of line 1110, and line 1130 represents the detrended temperature data from the pixel. As can be seen, line 1130 does not include the heating component of line 1110 thus improving the standard deviation calculation.

In step 716, the standard deviation of the detrended data is calculated for each pixel across the last M dynamics. The standard deviation of each pixel is then displayed as a temperature uncertainty map in step 718.

In step 720, the computer determines whether the user has attempted to modify the prostate boundary or the ultrasound applicator center location. In some embodiments, the prostate boundary can be modified regardless of the temperature uncertainty at a given point or pixel. If yes, the flow chart 70 proceeds to placeholder B, which also appears in FIG. 9. If not, the flow chart 70 proceeds to step 724 to determine if there's any indication that the prostate boundary may be too uncertain (e.g., due to motion or noise). If yes, the flow chart 70 proceeds to placeholder B. In addition, the system may trigger an alarm or pause the treatment if it determines that there's any indication that the prostate boundary may be too uncertain in step 724. If not, the flow chart 70 proceeds to placeholder C, which also appears in FIG. 10.

Figure 9:
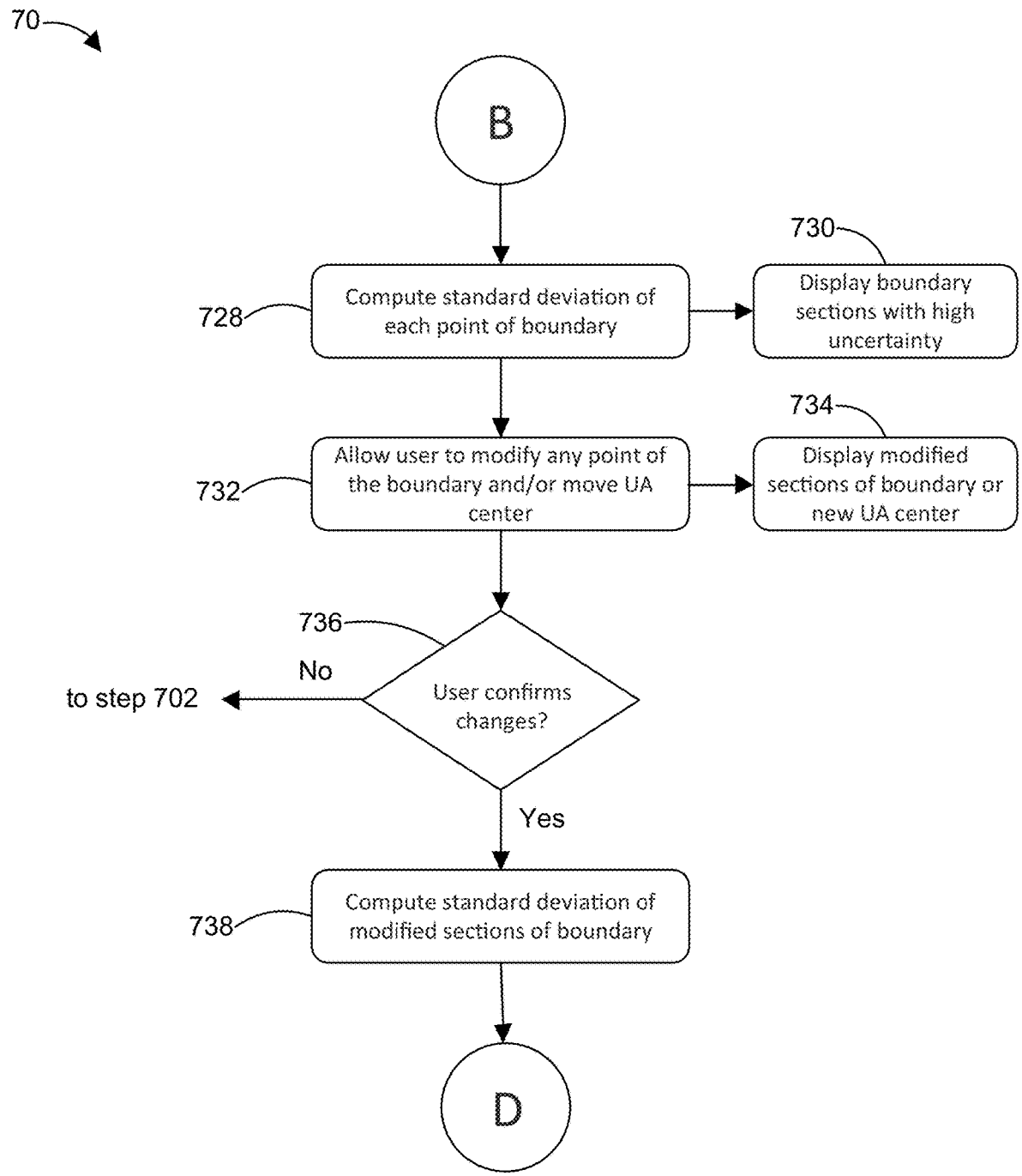

Starting at placeholder B on FIG. 9, the flow chart 70 proceeds to step 728 to compute the standard deviation of each point of the prostate boundary, similar to the manner described above. In step 730, the computer displays (e.g., on a color-coded map) the prostate boundary sections with high temperature uncertainty (e.g., greater than 2° C.).

In step 732, the user is allowed to modify any point on the prostate boundary and/or to move the ultrasound applicator center. In step 734, the modified sections of the prostate boundary and/or the new location of the ultrasound applicator are displayed.

In step 736, the user is asked to confirm the changes made in step 732 (i.e., the modifications to the prostate boundary and/or the ultrasound applicator center). If the user does not confirm the changes, the flow chart 70 returns to step 702 to receive a new dynamic. If the user confirms the changes, the flow chart 70 proceeds to step 738 where the standard deviation of the temperature in the modified sections of the prostate boundary is calculated. After step 738, the flow chart 70 proceeds to placeholder D, which appears in FIG. 10.

Figure 10:
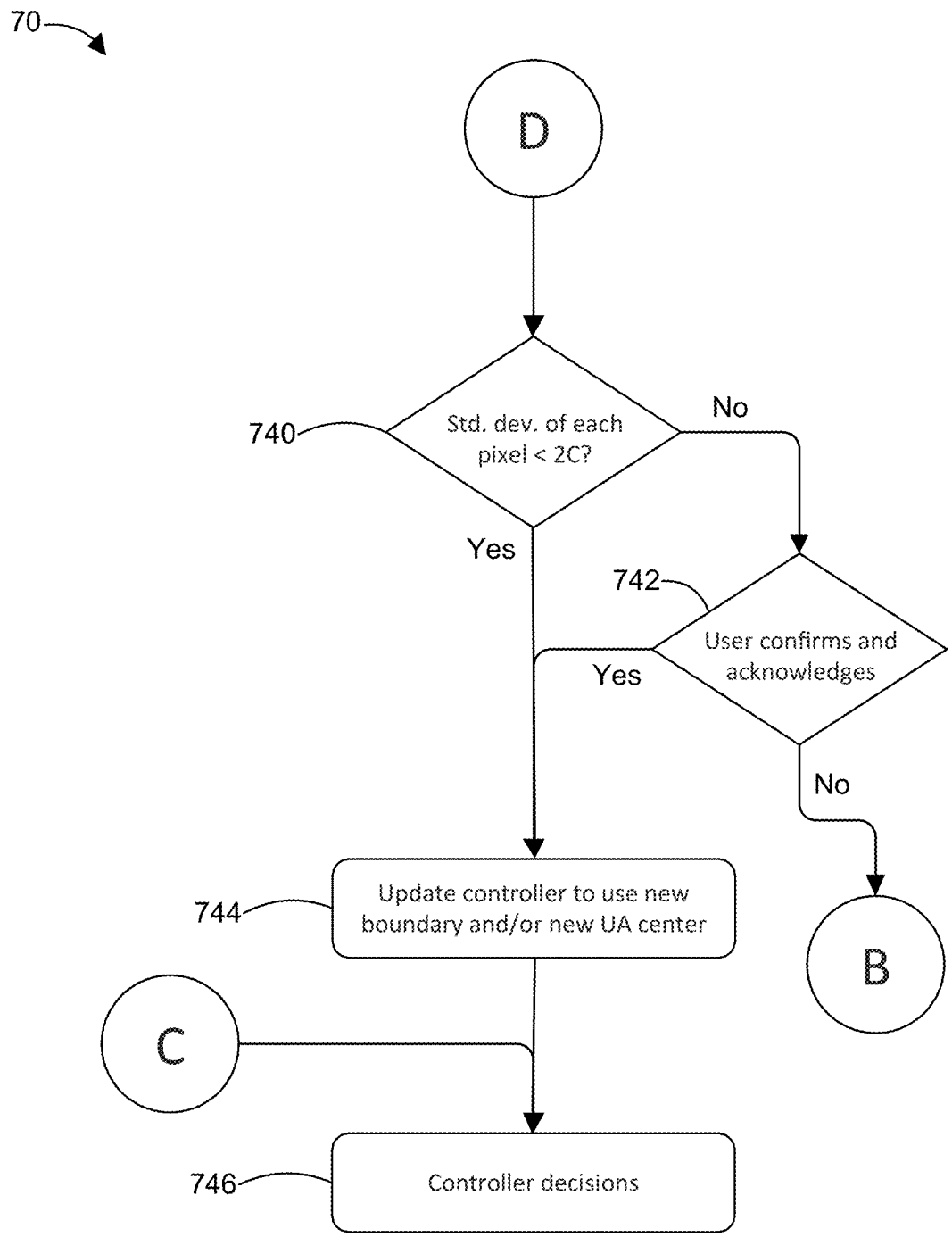

Starting at placeholder D on FIG. 10, the flow chart 70 proceeds to step 740 to determine if the standard deviation of each pixel is less than 2° C. If yes, the controller is updated to use the new prostate boundary and/or the new ultrasound applicator center, which were modified in step 732. If the standard deviation of any pixel is greater than or equal to 2° C. in step 740, the flow chart 70 determines whether the user has confirmed and acknowledged this large standard deviation at step 742. If the user has confirmed and acknowledged the large standard deviation, the flow chart 70 proceeds to step 744 to update the controller with the new prostate boundary and/or the new ultrasound applicator center, as discussed above. If the user has not confirmed and acknowledged the large standard deviation in step 742, the flow chart 70 returns to placeholder B in FIG. 9, at which point the standard deviation of each point of the prostate boundary is calculated in step 728. If sections of the modified prostate boundary are too uncertain (i.e., greater than 2° C.), the user can either (a) wait for the ultrasound applicator beam to pass if the user has modified a section currently being heated; (b) pause the treatment and wait for the temperature uncertainty map to stabilize; (c) re-draw the prostate boundary to a different location (e.g., to avoid the high temperature uncertainty region); (d) acknowledge and confirm that at least some sections of the prostate boundary have a high temperature uncertainty; or (d) discard the changes to the prostate boundary and continue with the original prostate boundary.

After the controller is updated in step 744, the flow chart 70 proceeds to step 746 for the controller to perform thermal therapy treatment based on the new boundary and/or new ultrasound applicator (UA) center (if coming from step 744) or based on the existing boundary and/or UA center (if coming from placeholder C). Flow chart 70 also proceeds to step 746 from placeholder C, which is reached after step 724, as discussed above.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A method for dynamically delivering thermal therapy to a target volume within a patient's body, comprising:

(a) determining an anatomical boundary corresponding to the target volume for delivery of thermal therapy thereto;
(b) using a thermal therapy applicator comprising an ultrasound transducer array, delivering a thermal therapy dose to said target volume;
(c) in a computer, receiving N sets of temperature data for pixels corresponding to a portion of a patient's body, each set of temperature data corresponding to a respective capture time of phase images captured using a magnetic resonance imaging (MRI) device, wherein N is greater than or equal to M, and M is a rolling capture time window;
(d) in the computer, for each of the past M capture times, determining a corrected temperature at each pixel;
(e) in the computer, for each pixel, calculating a temperature uncertainty based on said corrected temperature at each of the past M capture times
(f) in the computer, receiving a new set of the temperature data;
(g) in the computer, for the new set of temperature data, determining the corrected temperature at each pixel;
(h) in the computer, for each pixel, calculating an updated temperature uncertainty based on the past M capture times, the past M capture times including the new set of temperature data and excluding an oldest set of temperature data corresponding to an oldest capture time that was used to determine a last temperature uncertainty;
(i) repeating steps (f)-(h) to calculate, for each pixel, a dynamically updated temperature uncertainty while delivering the thermal therapy dose to said target volume;
(j) in the computer, receiving a request to modify a location of the anatomical boundary;
(k) in the computer, modifying the location of the anatomical boundary to a modified location;
(l) in the computer, determining if the dynamically updated temperature uncertainty for each pixel corresponding to the modified location of the anatomical boundary is below a threshold temperature uncertainty;
(j) generating an alert, with the computer, when the dynamically updated temperature uncertainty for the modified location of the anatomical boundary is greater than or equal to the threshold temperature uncertainty; and
(k) with the computer, automatically updating a thermal therapy controller with the modified location of the anatomical boundary when the dynamically updated temperature uncertainty for the modified location of the anatomical boundary is below the threshold temperature uncertainty.

2. The method of claim 1, wherein the temperature uncertainty and the updated temperature uncertainty correspond to a standard deviation of said corrected temperature at each pixel across the past M capture times.

3. The method of claim 1, further comprising pausing the delivery of the thermal therapy dose before modifying the location of the anatomical boundary.

4. The method of claim 1, further comprising:
receiving a request to modify a location of a thermal therapy applicator center;
in the computer, modifying the location of the thermal therapy applicator center to a modified center location;
with the computer, automatically updating the thermal therapy controller with the modified center location when the dynamically updated temperature uncertainty for the modified location of the anatomical boundary is below the threshold temperature uncertainty; and generating the alert, with the computer, when the temperature uncertainty for the modified location of the anatomical boundary is greater than or equal to the threshold temperature uncertainty.

5. The method of claim 1, further comprising, in the computer, validating the anatomical boundary to confirm that the dynamically updated temperature uncertainty for the modified location of the anatomical boundary is below the threshold temperature uncertainty.

6. The method of claim 5, further comprising, in the computer, calculating a standard deviation at each point along the anatomical boundary across the past M capture times.

7. The method of claim 1, further comprising, in the computer, generating a temperature uncertainty map, the temperature uncertainty map including the dynamically updated temperature uncertainty for each pixel.

8. The method of claim 7, further comprising displaying the temperature uncertainty map on a display coupled to the computer.

9. The method of claim 1, further comprising detrending the corrected temperature at each pixel across the past M capture times to form detrended temperature data.

10. The method of claim 9, further comprising performing a linear regression of the corrected temperature at each pixel across the past M capture times.

11. The method of claim 9, further comprising calculating a standard deviation of the detrended temperature data at each pixel.

12. The method of claim 11, further comprising determining the temperature uncertainty based on the standard deviation of the detrended temperature data at each pixel.

* * * * *